US00PP35606P2

(12) United States Plant Patent
Weisel

(10) Patent No.: US PP35,606 P2
(45) Date of Patent: Jan. 30, 2024

(54) ***DIPLADENIA* PLANT NAMED 'TSF 003'**

(50) Latin Name: *Dipladenia sanderi*
Varietal Denomination: TSF 003

(71) Applicant: TreeSap Farms LLC, Houston, TX (US)

(72) Inventor: Lawrence Harold Weisel, Carlsbad, CA (US)

(73) Assignee: Treesap Farms LLC, Houston, TX (US)

( * ) Notice: Subject to any disclaimer, the term of this patent is extended or adjusted under 35 U.S.C. 154(b) by 0 days.

(21) Appl. No.: 18/134,413

(22) Filed: Apr. 13, 2023

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./226, 232
See application file for complete search history.

(56) References Cited

U.S. PATENT DOCUMENTS

PP28,446 P3 * 9/2017 Kearley, Jr. ..... Plt./232

* cited by examiner

*Primary Examiner* — Karen M Redden
(74) *Attorney, Agent, or Firm* — Cassandra Bright

(57) ABSTRACT

A new and distinct *Dipladenia* cultivar named 'TSF 003' is disclosed, characterized by pink flowers and variegated foliage which has been proven stable. The variegated foliage has The new variety is a *Dipladenia*, typically produced as an indoor ornamental plant.

1 Drawing Sheet

Latin name of the genus and species: *Dipladenia sanderi.*
Variety denomination: 'TSF 003'.

BACKGROUND OF THE INVENTION

The new cultivar is a product of chance discovery. The new variety was discovered as a naturally occurring whole plant mutation of the unpatented *Dipladenia sanderi* 'Red Riding Hood', unpatented. The selection was made at a commercial nursery Mar. 1, 2020 in Escondido, California.

Asexual reproduction of the new cultivar 'TSF 003' was first performed at a commercial nursery in Escondido, California by terminal vegetative cuttings in April of 2020. Subsequent propagation has shown that the unique features of this cultivar are stable and reproduced true to type.

The following traits have been repeatedly observed and are determined to be the unique characteristics of 'TSF 003.' These characteristics in combination distinguish 'TSF 003' as a new and distinct *Dipladenia* cultivar:

1. Pink flowers.
2. Cream colored variegated margins of foliage.
3. Stability of variegation in successive vegetative propagation.

PARENT COMPARISON

Plants of the new cultivar 'TSF 003' are similar to the seed parent in most horticultural characteristics. The new variety, however, differs in the following:

1. The new variety has variegated foliage; the parent variety has solid colored foliage.

COMMERCIAL COMPARISON

'TSF 003' can be compared to compared to the commercial variety *Dipladenia* 'Madinia Pink', unpatented. Plants of 'Madinia Pink' are similar to plants of 'TSF 003' in most horticultural characteristics, however, plants of 'TSF 003' differ in the following:

1. 1. The new variety has variegated foliage; this comparator has solid colored foliage.

BRIEF DESCRIPTION OF THE PHOTOGRAPH

The accompanying drawing illustrates in full color typical plants of 'TSF 003' grown outdoors in Escondido, CA. This plants are approximately 12 months old, shown in an 1-gallon pots. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'TSF 003' plants grown outdoors in Escondido, CA. Temperatures ranged from 10° C. to 18° C. at night to 15° C. to 30° C. during the day. No artificial light, photoperiodic treatments were given to the plants. Measurements and numerical values represent averages of typical plant types.

Botanical classification: *Dipladenia sanderi* TSF 003'.

PROPAGATION

Time to initiate roots: About 15 days at approximately 30° C. in the summer. About 25 days at 18° C. in the winter.

Time to produce a rooted cutting: About 50 days at 20 to 30° C.

Root description: Freely branching and white-brown in color. Not accurately measured with R.H.S. chart.

PLANT

Growth habit: Vining evergreen flowering plant. Initially upright, then vining, requiring support to maintain upright habit. Typically, plants are pinched approximately 3 months after planting a rooted cutting to encourage branching.

Age of plant described: 10 months.

Container size: 1 gallon.

Height: Approximately 32 cm.

Plant spread: Approximately 21 cm.

Growth rate: Moderate.

Branching characteristics: Strong branching occurs after pinch.

Length of primary lateral branches: Approximately 10 to 15 cm.

Diameter of lateral branches: Approximately 4 mm.

Internode length: Approximately 15 to 24 mm.

Stem texture: Glabrous.

Color main lateral branches: Near RHS Green 143D.

FOLIAGE

Leaf:

*Arrangement*.—Opposite, simple.

*Average length*.—Approximately 6.5 cm to 8.0 cm.

*Average width*.—Approximately 3 cm to 4 cm.

*Shape of blade*.—Elliptic.

*Apex*.—Acute.

*Base*.—Obtuse.

*Attachment*.—Petiolate.

*Margin*.—Entire.

*Texture of top surface*.—Glabrous.

*Texture of bottom surface*.—Glabrous.

*Color*.—Young foliage upper side: Variegated: marginal region mostly Yellow 11C. Blotched and marbled in center, Green 137A, 138B and 138C. Very slightly flushed near Red 47C along margin. Young foliage under side: Variegated: marginal region mostly Yellow 11C. Blotched and marbled in center, Green 137A, 138B and 138C. Mature foliage upper side: Variegated: (4 to 8 mm), irregular marginal region mostly Yellow 11C. Blotched and marbled in center Green N138A, N138C, Green 137C. Mature foliage under side: Variegated: (4 to 8 mm), irregular marginal region mostly Yellow 11C. Blotched and marbled in center Green N138A, N138C, N138D.

*Venation*.—Type: Pinnate. Venation color upper side: Near RHS Yellow 11C. Lightly flushed Red 51D near base. Venation color under side: Near RHS Green 138C.

*Petiole*.—Average Length: Approximately 1.0 cm. Color: Upper surface near Yellow-Green 145C flushed Red 51C; lower surface near Yellow-Green 145C. Diameter: Approximately 2 mm. Texture: Glabrous.

FLOWER

Natural flowering season: Naturally flowers Summer through late Autumn.

Inflorescence type and habit: Single salverform flower; terminal or axillary; flowers face outward and upward.

Rate of flower opening: Approximately 3 days from bud to fully opened flower.

Flower longevity on plant: 4 to 5 days, after fully opened. Self-cleaning.

Quantity of flowers: Young plants have a range of 3 to 10 flowers and buds at all times.

Inflorescence size:

*Diameter*.—Approximately 6.2 cm.

*Length*.—Approximately 7.0 cm.

*Corolla tube length*.—Approximately 4.5 cm.

*Throat diameter*.—Approximately 1.5 cm.

Corolla:

*Petal arrangement*.—Single whorl of 5, fused into flared trumpet.

*Size*.—Lobe Length: 3.5 cm. Lobe Width: 2.5 cm.

*Margin*.—Entire.

*Apex*.—Acute.

*Texture*.—Smooth, velvety.

Color:

*Petals*.—When opening: Upper surface: Near RHS Red-Purple 63C, center flushed Red-Purple 64D. Lower surface: Near RHS Red-Purple 65C, center Red-Purple 63D. Fully opened: Upper surface: Near RHS Red-Purple 63C, center flushed Red-Purple 64D. Lower surface: Near RHS Red-Purple 65C, center Red-Purple 63D. Tube color (interior): Near RHS Yellow 8B and Yellow 13C with streaks near Red-Purple 63B. Tube color (exterior): Near RHS Yellow-White 158D with streaks near Red-Purple 63C and 63D.

Bud:

*Shape*.—Ovate to Lanceolate.

*Length*.—Approximately 5.3 cm.

*Diameter*.—Approximately 1.2 cm.

*Color*.—Base near Yellow-White 158D. Upper section near Red-Purple 63B.

Sepals:

*Arrangement*.—5 per flower in a single whorl; fused.

*Shape*.—Narrowly deltoid.

*Quantity*.—5.

*Length*.—Approximately 10 mm.

*Width*.—Approximately 2 mm.

*Margin*.—Entire.

*Apex*.—Acuminate.

*Texture*.—Smooth, waxy.

*Color*.—Upper surface: Near RHS Yellow-White 158B. Lower surface: Near RHS Yellow-White 158B.

Peduncles:

*Length*.—Approximately 1.5 cm.

*Width*.—Approximately 3 mm.

*Angle*.—Straight or slight undulation.

*Strength*.—Flexible and strong.

*Color*.—Near RHS Yellow-Green 145D.

Fragrance: None.

REPRODUCTIVE ORGANS

Stamens:

*Number*.—5, anthers fused together at tips, filaments fused to corolla.

*Anther length*.—1 cm.

*Anther color*.—Near RHS Yellow 13C.

*Anther shape*.—Oblong.

*Pollen*.—None observed.

Pistil:

*Number*.—1.

*Length*.—Approximately 2.5 cm.

*Style color*.—Near RHS Yellow-White 158B.

*Stigma*.—Shape: Globular. Color: Near RHS Orange-Red 34D. Ovary color: Near RHS Yellow-Green 145D.

OTHER CHARACTERISTICS

Disease resistance: Neither resistance nor susceptibility to normal diseases and pests of *Dipladenia* have been observed.

Drought tolerance and cold tolerance: Tolerates temperatures from approximately 0° C. to 40° C. and does not tolerate drought.

Fruit/seed production: Not observed.

What is claimed is:

1. A new and distinct cultivar of *Dipladenia* plant named 'TSF 003' as herein illustrated and described.

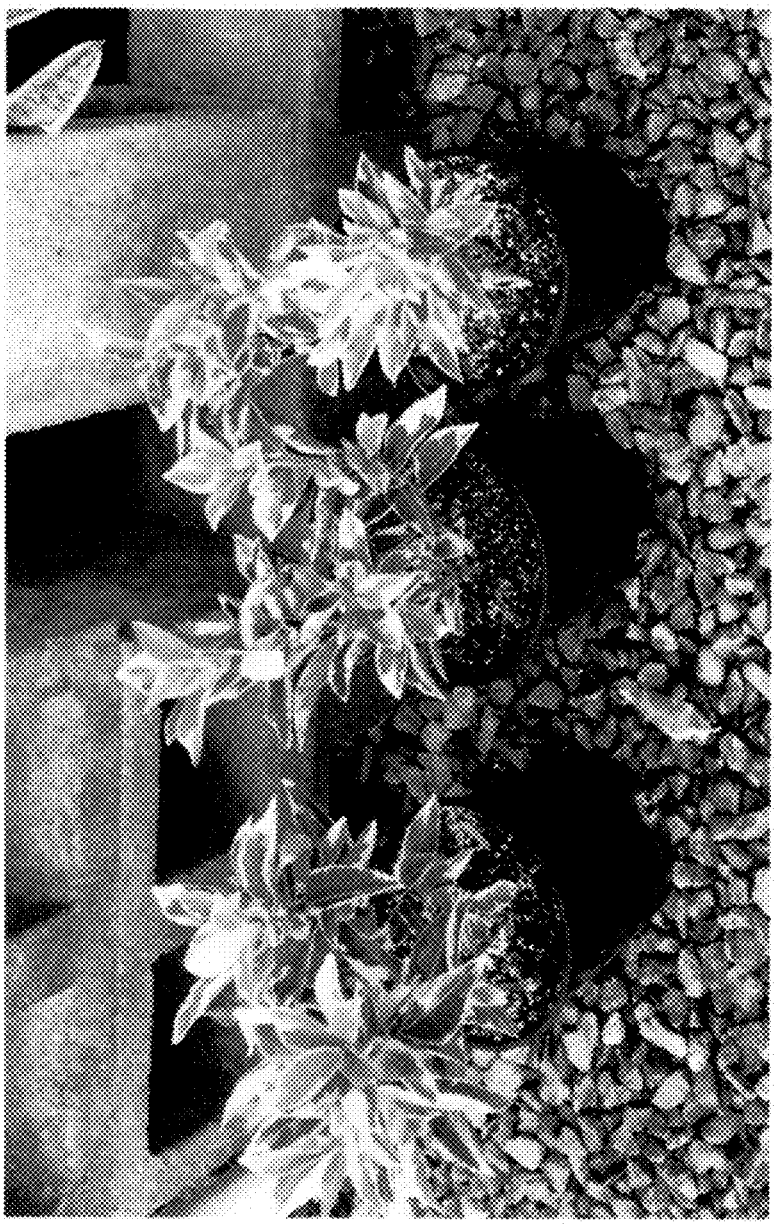

* * * * *